United States Patent [19]

Palepu et al.

[11] Patent Number: 5,011,022
[45] Date of Patent: Apr. 30, 1991

[54] CYCLIC FLOW SLURRY FRACTIONATION

[76] Inventors: Prakash T. Palepu, 2541 Overlook Rd., Apt. No. 6, Cleveland, Ohio 44106; Cheng-Kuang Wu, 376 Balmoral Dr., Richmond Heights, Ohio 44143; Robert J. Adler, 3068 Van Aken Blvd., Shaker Heights, Ohio 44120

[21] Appl. No.: 271,999

[22] Filed: Nov. 15, 1988

[51] Int. Cl.⁵ .......................... B03D 3/00; B01D 21/00
[52] U.S. Cl. .................................... 209/155; 209/209; 210/258; 210/513; 210/800
[58] Field of Search ............ 209/1, 132, 155, 156, 209/172, 173, 208, 209, 210; 210/258, 513, 800, 801; 364/502

[56] References Cited

U.S. PATENT DOCUMENTS

| 2,946,438 | 7/1960 | Belugou et al. | 209/156 |
| 4,043,760 | 8/1977 | Hiatt | 209/173 X |
| 4,066,536 | 1/1978 | Ball et al. | 209/155 |
| 4,250,026 | 2/1981 | Giddings et al. | 209/209 X |
| 4,280,823 | 7/1981 | Szonntagh | 209/1 X |
| 4,623,470 | 11/1986 | Adler | 210/787 |
| 4,737,268 | 4/1988 | Giddings | 209/210 X |

FOREIGN PATENT DOCUMENTS

0545389  3/1977  U.S.S.R. .............................. 209/156

Primary Examiner—Michael S. Huppert
Assistant Examiner—Edward M. Wacyra
Attorney, Agent, or Firm—Woodling, Krost and Rust

[57] ABSTRACT

Apparatus and methods are disclosed for separating or fractionating particles of differing sedimentation rates in a fluid. For fractionation, the mixture is introduced into a tube and subjected to a cyclic sequence of alternating axial flows, with optional waiting periods of zero flow. The velocities and time periods of the individual flows in the cycle are adjusted so that particles of greater and lesser sedimentation rates tend to be driven in opposite directions. At the end of each cycle there is a step of resuspension of sedimented particles without axial dispersion and independent of axial flows.

14 Claims, 7 Drawing Sheets

```
      ∇ SEPPROFILE;T;S;Z;X;XX;X1;X2;X21;X22;T1;T21;TT1;R;K;K1;K2;K3;K4;V;V1;V2;V3;
        V4;S;M1;M2;M3;MM1;MM2;M21;MOVES;W;Z1;Z2;D1;D2;D3;D4;D5;D6;DM;DV
[1]     MOVES← 16 48 32 ◊ T← 0.6 6 4 ◊ W← 0.9 0.6 0 ◊ V←MOVES÷T
[2]     D1←101ρ0 ◊ D2←D3←D4←D5←D6←(ρD1)ρ1250 ◊ S←254×1E¯4
[3]     R←0.375×2.54÷2 ◊ K←(0.03×980)×(S*2)÷18×9E¯3
[4]     V1←1.25×V[1] ◊ V2←2×V[2] ◊ V3←2×V[3] ◊ XX←ρX←ιρD1
[5]     'VELOCITIES ARE' ◊ V ◊ 'REYNOLDS NUMBERS ARE' ◊ 2×R×V÷9E¯3
[6]     K1←7×V1÷8×K×R*(1÷7) ◊ K2←V2÷R*2 ◊ K3←V3÷R*2
[7]
[8]     ⍝ LINES 1 THROUGH 6 SPECIFY THE PROBLEM. i.e. VARIOUS PARAMETER VALUES,
[9]     ⍝ DENSITIES, VISCOSITY AND OTHER SUCH INFORMATION IS ALSO SUPPLIED.
[10]    ⍝ LINES 14 THROUGH 36 EVALUATE PARTICLE MOVEMENTS IN THE 1ST (FORWARD)
[11]    ⍝ MOTION WHICH IS TURBULENT.  LINES 41 THROUGH 43 AND 48 THROUGH 50
[12]    ⍝ EVALUATE PARTICLE MOVEMENTS IN THE (LAMINAR)BACKWARD AND MAKEUP MOTIONS
[13]
[14]    Z1←D1 ◊ Z2←0.9525×(0,10×ι100)÷1000
[15]    ⍝ THEY (Z'S) ARE NOW ASSIGNED RADIAL POSITIONS IN THE TUBE
[16]    ⍝ GIVEN BY THE VECTOR Z2.
[17]    X1←(Z2≤R)/ιρZ2 ◊ X2←(Z2>R)/ιρZ2 ◊ T1←T[1]⌊Z2÷K
[18]    ⍝ X1 AND X2 ARE INDEX OF PARTICLES IN THE Z1 (OR Z2) VECTOR THAT
[19]    ⍝ ARE IN THE BOTTOM AND TOP HALF OF TUBE RESPECTIVELY.
[20]    T21←(Z2[X2]-R)÷K ◊ X21←(T1[X2]≤T21)/X2 ◊ X22←(T1[X2]>T21)/X2
[21]    ⍝ T21 IS THE TIMES THE PARTICLES IN THE UPPER HALF TAKE TO REACH R=0.
[22]    ⍝ X21 GIVES THE INDEX OF THOSE PARTICLES THAT STAY IN THE UPPER HALF.
[23]    ⍝ X22 IS THE INDEX OF PARTICLES THAT CROSS OVER FROM TOP HALF TO BOTTOM
[24]    ⍝ HALF OH THE TUBE. X1 AND X2 ARE INDICES FROM THE MAIN INDEX X.
[25]    TT1←(Z2[X22]-R)÷K
[26]    ⍝TT1 IS THE TIME THE CROSS OVER PARTICLES TAKE TO REACH R=0.
[27]    M1←K1×((Z2[X1]*8÷7)-((0⌈Z2[X1]-K×T1[X1])*8÷7))
[28]    ⍝ M1 IS THE DISTANCE TRAVELLED BY X1 PARTICLES, I.E., IN THE LOWER HALF.
[29]    M21←K1×((((2×R)+(K×T1[X21])-Z2[X21])*8÷7)-(((2×R)-Z2[X21])*8÷7))
[30]    ⍝ M21 IS THE MOVE BY THE PARTICLES THAT STAYED IN THE TOP HALF.
[31]    MM1←K1×((((2×R)+(K×TT1)-Z2[X22])*8÷7)-(((2×R)-Z2[X22])*8÷7))
[32]    ⍝ MM1 IS THE MOVE BY THE CROSS OVER PARTICLES IN THE TOP HALF ONLY.
[33]    MM2←K1×((((ρX22)ρR)*8÷7)-((((ρX22)ρR)-K×(T1[X22]-TT1))*8÷7))
[34]    ⍝ MM2 IS THE MOVE BY THE CROSS OVER PARTICLES IN THE BOTTOM HALF ONLY.
[35]    Z1[X1]←Z1[X1]+M1 ◊ Z1[X21]←Z1[X21]+M21 ◊ Z1[X22]←Z1[X22]+MM1+MM2
[36]    Z2←0⌈Z2-T1×K ◊ D3←Z1 ◊ D4←Z2
[37]    ⍝ THE MOVEMENTS AND RADIAL POSITIONS ARE ASSIGNED FOR THE 1ST MOTION.
[38]
[39]    D4←0⌈D4-W[1]×K ◊ ⍝ THIS IS THE 1ST WAITING PERIOD (TFB)
[40]
[41]    T1←T[2]⌊D4÷K
[42]    M2←K2×((2×R×D4×T1)+(K×(D4-R)×T1*2)-(T1×D4*2)+((K*2)×(T1*3)÷3))
[43]    D5←D3-M2 ◊ D6←0⌈D4-T1×K
[44]    ⍝ THE MOVEMENTS AND RADIAL POSITIONS ARE ASSIGNED FOR THE 2ND MOTION.
[45]
[46]    D6←0⌈D6-W[2]×K ◊ ⍝ THIS IS THE 2ND WAITING PERIOD. (TBM)
[47]
[48]    T1←T[3]⌊D6÷K
[49]    M3←K3×((2×R×D6×T1)+(K×(D6-R)×T1*2)-(T1×D6*2)+((K*2)×(T1*3)÷3))
[50]    D1←D5+M3 ◊ D2←0⌈D6-T1×K
[51]    ⍝ THE LENGTHS AND RADIAL POSITIONS ARE ASSIGNED FOR THE 3RD MOTION.
[52]
[53]    D2←0⌈D2-W[3]×K ◊ ⍝ THIS IS THE 3RD WAITING PERIOD, NORMALLY 0.
[54]
[55]    DM←(+/D1)÷ρD1 ◊ DV←(+/((DM-D1)*2))÷ρD1
[56]    'MEAN AND VARIANCE ARE' ◊ DM,DV
      ∇
```

Figure 5

| | Independent Parameters | | | | Dependent Parameters | | | | | | | | | | Large Particles | | Small Particles | |
|---|---|---|---|---|---|---|---|---|---|---|---|---|---|---|---|---|---|---|
| N | $R_1$ | $R_2$ | $R_3$ | $R_4$ | $x_F$ | $x_B$ | $x_M$ | $t_F$ | $t_{FB}$ | $t_B$ | $t_{BM}$ | $t_M$ | $u_F$ | $u_B$ | $u_M$ | Mean | Var | Mean | Var |
| 54 | 0.33 | 0.43 | 1.5 | 0.1 | 16 - 48 | 32 | 0.6 | 0.9 | 6.0 | 0.6 | 4.0 | 26.7 | -8.0 | 8.0 | 11.1 | 58 | -11.0 | 697 |
| 29 | 0.33 | 0.43 | 1.5 | 0.1 | 30 - 90 | 60 | 0.6 | 0.9 | 6.0 | 0.6 | 4.0 | 15.0 | -4.5 | 4.5 | 20.9 | 204 | -20.6 | 2450 |
| 96 | 0.33 | 0.43 | 1.5 | 0.1 | 9 - 27 | 18 | 0.6 | 0.9 | 6.0 | 0.6 | 4.0 | 50.0 | -15.0 | 15.0 | 6.3 | 18 | -6.2 | 220 |
| 54 | 0.44 | 0.43 | 1.5 | 0.1 | 21 - 48 | 27 | 0.6 | 0.9 | 6.0 | 0.6 | 4.0 | 35.0 | -8.0 | 6.8 | 16.2 | 71 | -5.7 | 695 |
| 54 | 0.25 | 0.43 | 1.5 | 0.1 | 12 - 48 | 36 | 0.6 | 0.9 | 6.0 | 0.6 | 4.0 | 20.0 | -8.0 | 9.0 | 7.1 | 51 | -15.2 | 699 |
| 54 | 0.33 | 0.50 | 1.5 | 0.1 | 16 - 48 | 32 | 0.7 | 1.05 | 5.77 | 0.58 | 4.0 | 22.9 | -8.3 | 8.0 | 12.3 | 47 | -9.7 | 690 |
| 54 | 0.33 | 0.30 | 1.5 | 0.1 | 16 - 48 | 32 | 0.42 | 0.63 | 6.4 | 0.65 | 4.0 | 38.1 | -7.5 | 8.0 | 8.7 | 84 | -13.3 | 695 |
| 54 | 0.33 | 0.43 | 2.0 | 0.1 | 16 - 48 | 32 | 0.5 | 1.0 | 6.0 | 0.6 | 4.0 | 53.0 | -8.0 | 8.0 | 11.8 | 62 | -10.8 | 705 |
| 54 | 0.33 | 0.43 | 0.5 | 0.1 | 16 - 48 | 32 | 1.0 | 0.5 | 6.0 | 0.6 | 4.0 | 16.0 | -8.0 | 8.0 | 10.2 | 52 | -11.4 | 667 |
| 54 | 0.33 | 0.43 | 1.5 | 0.5 | 16 - 48 | 32 | 0.6 | 0.9 | 4.4 | 2.2 | 4.0 | 26.7 | -10.9 | 8.0 | 9.3 | 94 | -19.0 | 1061 |
| 54 | 0.33 | 0.43 | 1.5 | 0.0 | 16 - 48 | 32 | 0.6 | 0.9 | 6.0 | 0.6 | 4.0 | 26.7 | -6.6 | 0.0 | 11.6 | 51 | -8.5 | 579 |

Figure 6

| Exp. type | Particle Size microns | Particle Density gm/ml | $u_{SS}$ $u_{SL}$ cm/s | $u_F$ cm/s | $t_F$ s | $t_{FB}$ s | $u_B$ cm/s | $t_B$ s | $t_{EM}$ s | $u_M$ cm/s | $t_M$ s | Avg. Move per Cycle cm | $u_{FD}$ cm/s | $t_{FD}$ s | Avg. Move per Feed cm |
|---|---|---|---|---|---|---|---|---|---|---|---|---|---|---|---|
| Batch Exp. | 254 | 1.03 | 0.105 | 31.58 | 0.6 | 0.98 | −8.42 | 6.25 | 1.0 | 8.42 | 4.0 | −13.05 | Not Applicable for Batch Experiments | | |
| | 137 | 1.24 | 0.240 | 31.58 | 0.6 | 0.98 | −8.42 | 6.25 | 1.0 | 8.42 | 4.0 | 13.00 | | | |
| Cont. Exp. | 254 | 1.03 | 0.105 | 31.58 | 0.6 | 0.98 | −8.42 | 6.25 | 1.0 | 8.42 | 4.0 | −13.05 | 15.79 | 0.5 | 10.48 |
| | 387 | 1.03 | 0.240 | 31.58 | 0.6 | 0.98 | −8.42 | 6.25 | 1.0 | 8.42 | 4.0 | 13.00 | 15.79 | 0.5 | 10.36 |

Fluid is water for all operations.
See text for explanation of nomenclature

Figure 7

CYCLIC FLOW SLURRY FRACTIONATION

BACKGROUND OF THE INVENTION

There is a need in industry for separating fine particles according to their size, shape and/or density. In countercurrent solid-liquid extraction processes, it is necessary to move particles and liquid in opposite directions. Some examples of particle fractionation are cleaning of coal slurries where heavier pyrite particles containing sulphur are removed from coal, fractionation of chromatography packing materials into narrow size ranges in order to limit axial dispersion of the species to be separated, and separation of ceramic materials into fractions with narrow particle size distributions to enhance strength and uniformity of sintered parts. Examples of countercurrent extraction are decaffeination of coffee beans, hydrometallurgical extractions, and extraction of edible oils from oil seeds using hexane.

The prevalent methods used for particle size fractionation are screening, centrifugal sedimentation and flotation. Each of the above methods is best suited to a different range of particle sizes and types with considerable overlap among them. As the particle size decreases below 100 $\mu$m, separation becomes difficult. Most physical separation techniques lose their effectiveness in this range and surface chemical differences or particle motion in an induced field such as a centrifugal or magnetic field becomes the basis for separations. In general, only high speed centrifuges are effective for separations below 10 $\mu$m. However, their costs are high due to their mechanical complexity.

Sharp separations and high product purities are rarely achieved because all the above techniques are inherently single stage separation operations. Staging involves installing additional hardware with associated increases in capital and operating costs. Recycling is difficult, and for centrifugal separations, it is energy intensive. Hence in most processes only a few stages are employed. In addition, the flexibility of these classical methods is somewhat limited; changes in particle characteristics often require hardware modifications.

Two more modern separation techniques are of especial interest since they are more closely related to the present invention than the general methods discussed above. These techniques are parametric pumping and field-flow fractionation.

The process known as parametric pumping is a relatively new concept in separation processes. The technique is generally credited to Wilhelm and his coworkers although the method was apparently conceived earlier under the name "Heatless Distillation" by Skarstrom. In this technique cyclic changes in some intensive variable like temperature, pressure, or pH periodically shift the equilibrium distribution of solute between two phases. The modest composition differences induced are amplified and organized into useful separations by coupled, cyclic, bi-directional flows. In parametric pumping the cyclic flow change and intensive variable change are out of phase.

The number of stages in a small apparatus can be very large and dramatic separations and purities of adsorbed species can be achieved. The main limiting factor of parametric pumping is the slowness inherent in the molecular diffusion steps of heat and mass transfer in large scale equipment. One notable exception is pressure swing absorption which has cycle times on the order of a few seconds.

Another separation technique related to our method is field-flow fractionation (FFF) pioneered by J. C. Giddings and his coworkers for chromatographic separations. A field acts perpendicular to flow in a narrow channel, forcing particles toward a wall. Simultaneously, diffusion disperses the particles in the channel cross section. Particles least affected by the field and most affected by diffusion are swept downstream preferentially by the axial flow. Particles most affected by the field concentrate near the wall and move downstream slowly due to smaller axial velocities near the wall. A pulse of a mixture of particles will emerge in several fractions or peaks as in chromatography.

Giddings and others employed various external fields such as thermal, pressure gradient across membrane walls, magnetic, and centrifugal. A recent survey of FFF separation techniques was made by Janca (Janca, J., *Field-Flow Fractionation: Analysis of Macromolecules and Particles*, Marcel Dekker, Inc., New York (1988)). For the most part, work on FFF has been concentrated on the use of the technique as an analytical laboratory tool.

Several years ago one of the inventors herein developed a technique (U.S. Pat. No. 4,623,470 to Dr. Robert J. Adler) based on the concept of combining two factors: (1) a steady separative force which acts to produce a concentration gradient perpendicular to the walls of the containing tube, such as a steady centrifugal, magnetic, or electric field, and (2) periodic flow through the tube composed of cycles containing at least one step of forward flow and one step of backward flow, and usually also a step of zero flow, where the periodic flow and geometry are such as to interact to produce periodic local mixing, as for example flow through a curved tube which induces secondary flows perpendicular to the tube wall, or asymmetric flows through a straight tube which are periodically laminar and turbulent. The basic phenomena bringing about the separation are presumed to be migration of species perpendicular to the tube wall under the influence of the separative force which causes one or more species to concentrate along a solid surface in each cross section, and convective transport of particles, droplets, or molecules along the tube by the imposed periodic flows.

Thus, the method described above differs from parametric pumping in that it uses a steady separative force perpendicular to the tube axis rather than a periodic one or steady one varying along the tube axis, and specially modulated and controlled back-and-forth flows rather than symmetric periodic flows. The special back-and-forth flows bring about local periodic mixing and resuspension of the species being separated or fractionated, and also transport the species being separated along the conduit in which the process is being conducted. The local periodic mixing is enabled by a curved conduit, such as a helical tube, and/or flows which are asymmetric in their velocity. A species mixed or suspended in the fluid is transported by the motion of the fluid in one direction, and when the same species is adjacent to a solid boundary the other components are transported by the fluid in the opposite direction.

That method somewhat resembles sedimentation FFF, in which the flow channel is a helical tube within a centrifuge bowl, but it differs from FFF in that rapidly alternating rather than fundamentally unidirectional flows are used, and in that the separated products are produced essentially in a steady fashion at opposite ends of the apparatus, while in FFF the products are produced in an essentially sequential series of pulses at one end of the apparatus. Also, periodic secondary flows are employed advantageously as an essential part of the process, rather than being suppressed as is critical to FFF.

As claimed in the Adler patent, sedimentation is enhanced by centrifugal force about an axis of rotation of an elongated (preferably helical) chamber. For example, to separate a slurry into a concentrated fraction and a lean fraction, the basic process for a batch operation is as follows. Each cycle of periodic operation consists of three steps: step "a" of zero flow; step "b" of flow in a first direction through the helical tube; and a step "c" of flow in a second (opposite) direction through the helical tube. The steps are sequential and form a cycle which is repeated indefinitely to bring about the separation. Throughout all of the steps and cycles the helical tube spins steadily about its axis causing the slurry contained in the tube to be subjected to a constant centrifugal force field.

During step "a" the centrifugal force causes particles to move radially outward toward the outer wall of the helical tube, i.e. the portion of the tube wall farthest from the helical tube axis, where they become relatively concentrated.

In step "b", fluid is transported by pumping in a first direction through the helical tube. Generally the volume pumped is less than the volume of the helical tube. During the initial part of step "b" the particles continue to be located adjacent to the tube wall and are therefore temporarily immobilized with respect to axial flow. Thus the fluid moved along the helical tube by the pumping is relatively free of particles. As time passes within step "b", the axial flow begins to induce secondary flows or cross currents within the helical tube which resuspend the fine particles that had been concentrated along the outer wall of the tube. Step "b" is terminated when the developing secondary flows have resuspended the particles.

In step "c", the flow is reversed through the helical tube by pumping in the opposite direction. Generally the volume of fluid displaced is again at most the volume of the helical tube. Secondary flow again keeps the particles substantially resuspended so the particles are carried backwards with the fluid.

Separation occurs because the fluid moving in step "b" in a first direction is substantially free of particles while fluid moving in step "c" in the second (opposite) direction is relatively concentrated in particles. In other words, the particles lag behind the axial fluid motion in step "b", but move more nearly in phase with the axial fluid motion in the reverse direction in step "c". The repetition of cycles consisting of steps "a", "b" and "c" enable even a slight amount of separation in the cross sections to be cascaded into a large separation between the ends of the tube. Liquid accumulates free of fine particles in the reservoir adjacent the end of the helical tube toward which the flow is directed in step "b", and concentrated slurry accumulates in the reservoir adjacent the opposite end of the helical tube toward which the flow is directed in step "c".

Different sequences of steps with different step durations in the cycles enable slurries to be fractionated into portions according to particle size or density and enable emulsions or molecular mixtures to be separated or fractionated. This is because step "a" causes faster sedimenting particles preferentially to settle out, and they are left behind, relative to slower sedimenting particles, in step "b". They must then be resuspended by the flow in step "b" so that the repeated cycles will result in an accumulating separation.

The Adler patent also discusses (column 13, line 43 to column 14, line 9) the extension of the technique to a straight tube by making the forward and backward flows asymmetric in their flow rates. According to that disclosure, the fast flow should be the one that accomplishes the resuspension of particles, while the slower, reverse flow should not be a mixing one.

It has been found, however, that the process disclosed in the Adler patent for a straight tube was not adequately effective to separate the resuspension step from the reverse flow step; and that as a result the separation technique of the Adler patent is not as suitable for use with a straight tube. In fact, even in a curved tube, in which resuspension is to be achieved by secondary flows generated by the axial flows, resuspension is inadequate. That is, whether generated by secondary flow and/or turbulence in a curved tube or by turbulent flow in a straight one the resuspension mechanism of the Adler patent is not sufficiently vigorous nor easy to control. A need, therefore, existed for a way to adapt the Adler concept for use in any tube, and obtain better separations.

SUMMARY OF THE INVENTION

The present invention, like that of the Adler patent, is a method of fractionating slurries using the alternating axial flows of parametric pumping, but with a steady separative force. The periodic axial flows are coupled with a field effect, namely gravitational sedimentation, to effect separations. Thus the positive aspects of parametric pumping such as high degree of separation are retained while the disadvantages of a diffusion limited rate process are avoided.

The separation of particles according to their sedimentation rate takes place in a long, thin, horizontal tube. The process consists of repeated periodic cycles in which particles settle and subsequently are resuspended in the tube cross section. Coordinated with the sedimentation and resuspension are forward and backward flows of the slurry in the axial direction of the tube.

Consider the tube initially filled with a dilute slurry composed of two types of particles, "A" and "B", and a low viscosity fluid such as water. The particles sizes and densities are such that the "A" particles sediment faster than the "B" particles. Cyclic repetition of a series of process steps causes the initially uniform slurry to separate into pure "A" slurry at the right end of the tube and pure "B" slurry at the left end of the tube.

Many different process cycles are possible. They all contain periods of time when the particles are uniformly suspended, partially sedimented, and fully sedimented. The cycle begins with uniform suspension of all of the particles in each cross section of the tube. While the particles are uniformly suspended, axial flow to the right causes both "A" and "B" particles to move rightward. While the particles are partially sedimented, slurry richer in slower settling "B" particles is moved leftward by axial flow. The faster settling "A" particles are less affected by this leftward motion because they are more fully sedimented than the "B" particles. When all the particles are fully sedimented, fluid alone is moved either leftward or rightward to achieve zero net fluid flow over a cycle. With appropriate axial flows, the overall effect of each cycle is that the "A" particles move preferentially rightward, the "B" particles move preferentially leftward, and there is no net flow of fluid.

At the end of the cycle, the particles are resuspended in a manner which minimizes axial mixing, and a new cycle begins. An important feature of our invention is the use of a resuspension mechanism independent of axial flows. As described above, Adler (U.S. Pat. No. 4,623,470) teaches resuspension by axial flow induced secondary flows in curved conduits and also resuspension induced by turbulent flow in straight tubes. To achieve significant particle resuspension using these methods requires excessively long axial motions and times, causing large amounts of axial dispersion of the particles being separated. The resulting sharpness of separation is severely limited as has been observed experimentally. (Papanu, J. S., R. J. Adler, M. B. Gorensek, and M. M. Menon "Separation of Fine Particle Dispersions Using Periodic Flows in a Spinning Coiled Tube," AIChE J., 32 (5), 798 (1986).)

Thus, it is essential to have an effective and controllable resuspension mechanism superior to the poor resuspension provided by axial flows. An effective method of particle resuspension independent of axial flows is inverting the separator tube with respect to a gravitational or other field. This method of resuspension was used in the example experiments reported hereunder. Other mechanisms can also be used, as well understood by those familiar with the art of particle separations. These include, but are not limited to, acoustic methods.

The step of resuspension has been modeled by assuming randomization of positions of particles to achieve uniform particle concentrations in the tube cross section located at the axial position where sedimentation occurred. The purpose of resuspension is to reposition the particles away from their sedimented positions so as to enable them to sediment again in the next cycle. Any particle distribution in the tube cross section which positions the particles substantially away from their sedimented position is acceptable. The random repositioning of particles is but one example of an acceptable distribution. Another and more useful distribution upon resuspension is positioning all of the particles diametrically opposite to their original sedimented positions as occurs with field inversion resuspension.

Extremely sharp separations are enabled (even if "A" and "B" differ only slightly in their settling rates) by repeating the cycle many times. The process can be batch or continuous. For continuous operation, feed and product withdrawal steps are added.

It is an object of the present invention to provide a process and apparatus for separating and fractionating particles in a fluid.

Another object of the invention is to provide such a process which is continuous but periodic, for separating particles according to their size and/or density.

A further object of the invention is to provide such apparatus which is economical and which is adapted for either batch or continuous processing as desired.

Other objects and a greater understanding of the invention will appear from the claims appended hereunto taken together with the specification and figures in which

FIGS. 3a through 3d are graphical representations of the positions of particles located originally at the same axial position in a tube of our apparatus, after each step in a preferred embodiment of the process of the present invention:

FIGS. 4a and 4b are graphical representations showing the average movement of particles in two embodiments, batch and continuous:

FIG. 5 is a computer program in APL programming language of a simulated cycle in an embodiment of the process;

DESCRIPTION OF A PREFERRED EMBODIMENT OF THE INVENTION

Figure 1:
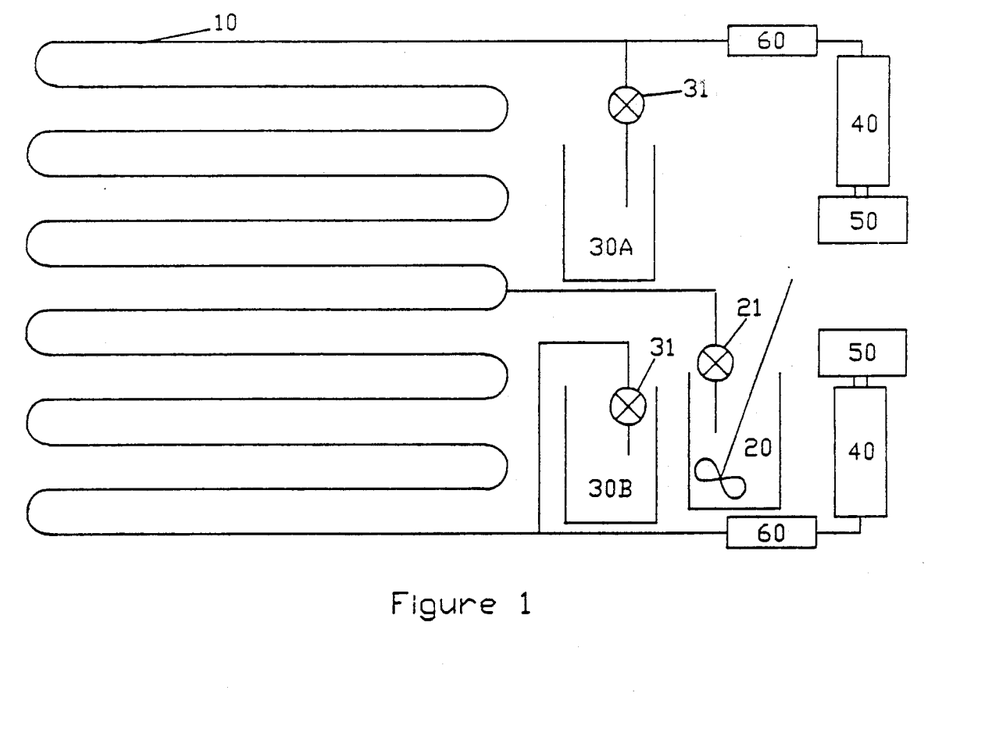
FIG. 1 is a schematic drawing of the apparatus of the present invention.
Figure 2:
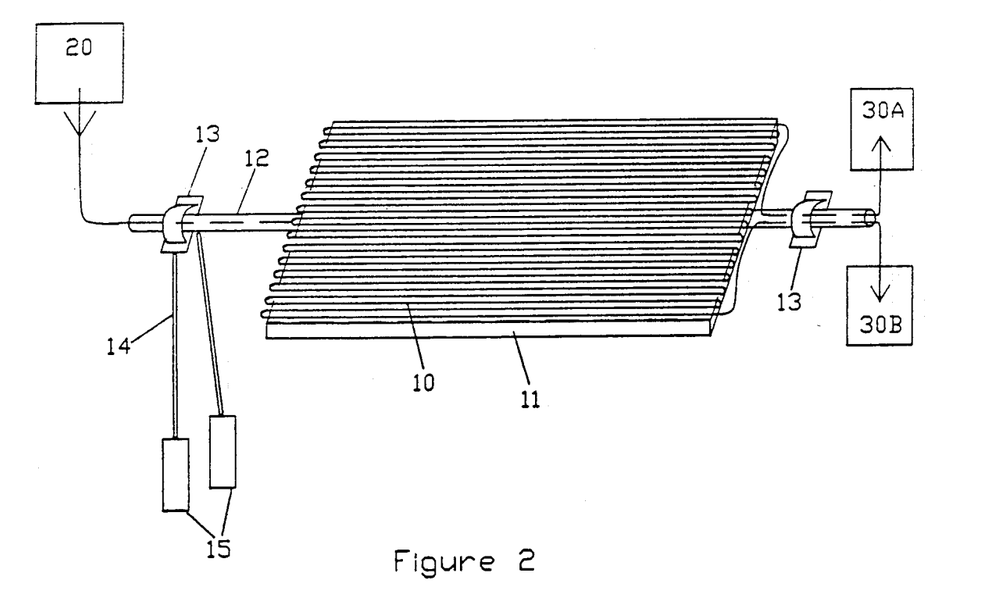
FIG. 2 is a simplified perspective drawing of a preferred embodiment of the apparatus.

The process of the present invention has been demonstrated by a simple apparatus shown schematically in FIG. 1 and in simplified perspective in FIG. 2.

A separator tube 10 of polyurethane flexible tubing, 26 m long and 0.95 cm I.D., is wrapped around a flat plate 11 which is mounted on a shaft 12 supported on two pillow blocks 13. A gear and chain mechanism 14 connects the shaft 12 to two air cylinders 15 which allow the shaft/flat plate/tube assembly to be rotated (flipped) about its longitudinal axis by 180°. This rotation resuspends sedimented particles. The tube actually used was circular in cross section, but it will be clear that any shape of cross section permitting resuspension may be used. The diameter of the tube (whereby "diameter" is meant the minimum cross section dimension) may be any convenient size at least four times the largest particle size.

Feed slurry containing the particle mixture is introduced into the middle of the tube by feed means 20 and products are withdrawn from the ends by product collection means 30A, 30B. The ends of separator tube 10 are also connected to piston pumps 40 operated by stepping motors 50. Pistons pumps 40 are used for creating axial flows in the tube. In-line filters 60 are used just before the piston pumps so that no particulate matter enters the piston pumps. Solenoid operated pinch valves 21 and 31 are used to open and close feed and output lines.

Feed is introduced by opening a feed valve 21, closing output valves 31 and moving either one or both pistons (not shown) backward. Product output is achieved by reversing the above actions. When all three valves are closed, the tube 10 and piston pumps 40 form a closed system and material inside tube 10 can be moved to the left or right by appropriate piston movements.

Tube volume is 1.78 l (0.95 cm I.D., 26 m long) and maximum piston displacement is 300 ml. Piston pumps 40 can generate a maximum average velocity of 210 cm/s ($N_{Re} = 20,000$ for water) inside the tube and the velocity can be controlled to within ±2 cm/s by the stepping motors 50. All valve positions, piston movements and flipping (rotation) of the tube assembly are controlled and monitored by a personal computer, not shown.

A critical aspect of the apparatus design is the length of the separator tube. The length should be chosen sufficiently long to control axial dispersion of the fractionated species in order to achieve the desired sharpness of separation. The concentration profile of a separated species as a function of axial position Z, average drift velocity U, and axial dispersion coefficient D is given by:

$$C = (|U|/D) * \mathrm{Exp}(-|U_i||Z|/D)$$

The values of U and D are obtained from the simulation of a cycle to be described. The tube length L should be chosen long enough to cause the concentration of a separated species to be as small as desired at the lean end (the end opposite to the species withdrawal end).

A three step sequence typical of the process of the present invention—perhaps the simplest member of a large family of possible sequences—will now be described in detail, as modeled by the inventors herein (Palepu, P. T., C. Wu, and R. J. Adler "Modeling of Periodic Flow Slurry Fractionation", a paper presented at the AIChE Annual Meeting, New York, N.Y., November 1987; Adler, R. J., P. T. Palepu, and C. Wu, "Periodic Flow Slurry Fractionation", Proceedings of Conference for the Process Industries, CHEMECA '88, Sydney, Australia, August 1988). Particles with higher sedimentation rates are denoted by "A" and those with lower sedimentation rates are denoted by "B". Sedimentation rates depend on particle size and density difference between particles and fluid.

Figure 3A:
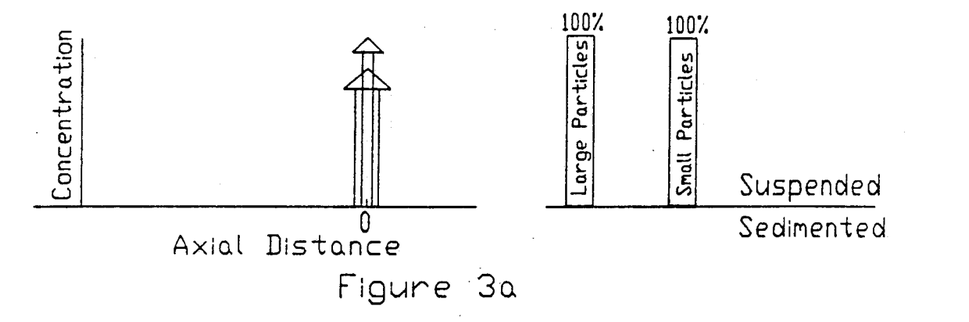
FIG. 3a shows the initial particle positions.

Initially "A" and "B" particles are completely mixed and randomly distributed in the cross sections of the tube. FIGS. 3a through 3d are provided to illustrate the particle distributions generated by the operation of a single three step cycle upon the particles originally suspended at a single axial point which for convenience is set at 0. FIG. 3a shows two superimposed pulses containing "A" and "B" particles respectively at that axial position. All of the particles are initially suspended.

Figure 3B:
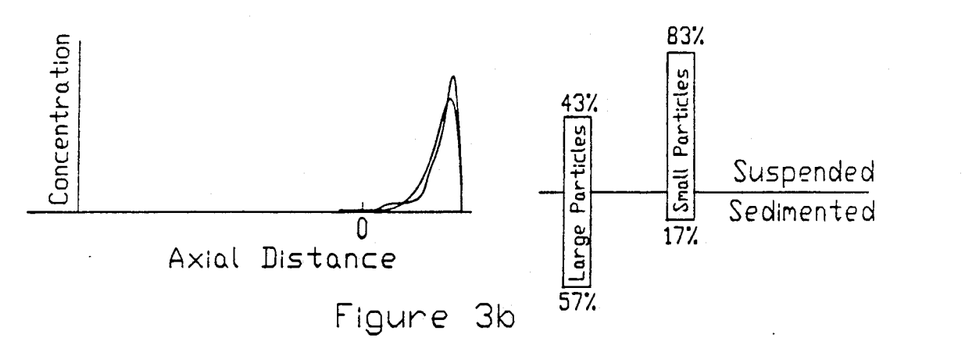
FIG. 3b shows the particle positions after the first step.

In step one, a volume $V_1$ of slurry is pumped rapidly from left to right. This movement is fast and all of the particles move to the right. This motion is followed by an optional waiting period with no axial movement. Typical axial distributions of "A" and "B" particles and the percent of the particles sedimented after the waiting period are shown in FIG. 3b. At the end of step one (forward flow plus the associated waiting period) a significant portion of the "A" particles has completely sedimented due to their higher sedimentation rate while most of the "B" particles remain suspended.

Figure 3C:
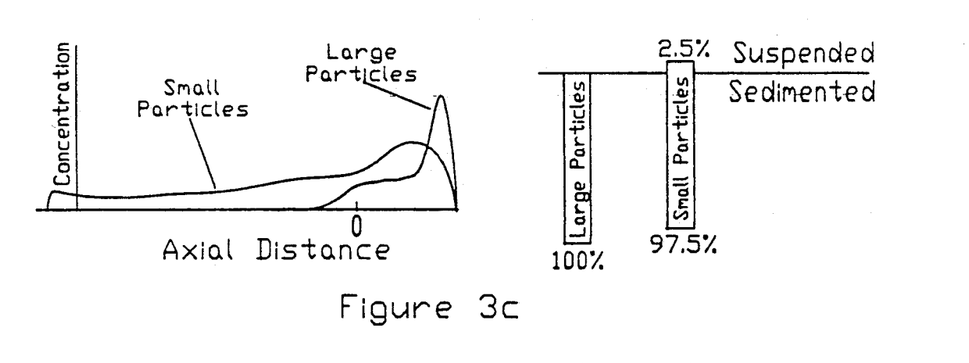
FIG. 3c shows the particle positions after the second step.

In step two a volume $V_2$ is pumped from right to left and all particles still in suspension are moved to the left. Normally volume $V_2$ is greater than $V_1$ and the velocity is slower than that of rightward motion in step one. This is followed by a second optional waiting period long enough to sediment most of the remaining particles. The axial concentration distribution of the "A" and "B" particles after the second waiting period is shown in FIG. 3c. The "A" particles are relatively unaffected by the leftward motion since most of them are completely sedimented or nearly sedimented prior to the start of the leftward motion, while most of the "B" particles move leftward. As depicted in FIG. 3c, all the "A" particles and most of the "B" particles have completely sedimented by the end of step two.

Figure 3D:
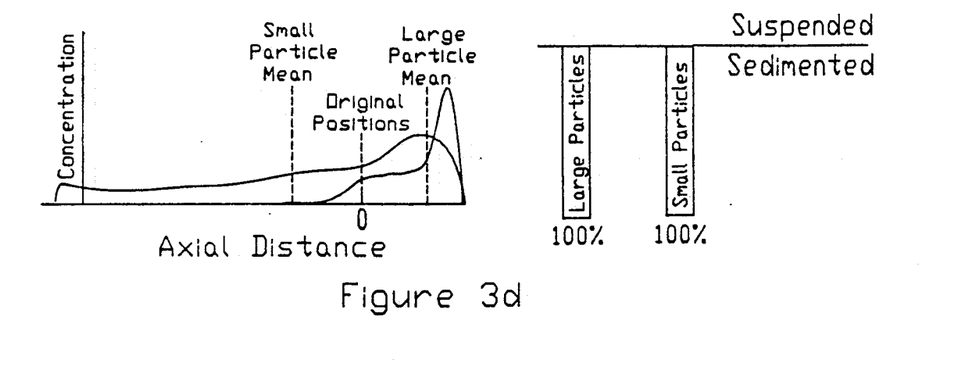
FIGS. 3d shows the particle positions after the third step.

Step three is one of make-up fluid motion. A volume $V_M = V_2 - V_1$ is pumped slowly from left to right without disturbing the settled particles. This step, which completes the cycle, is ordinarily used to insure that there is no net movement of fluid per cycle. In some situations a net flow of slurry or fluid per cycle through the tube is desirable. In these situation, the make-up stroke volume $V_M$ is chosen in conjunction with $V_1$ and $V_2$ to achieve the desired net flow.

FIG. 3d shows the axial concentration profiles of "A" and "B" particles at the end of the cycle. Separation has occurred in the sense that the means of the axial distributions of the "A" and "B" particles have moved to the right and left respectively from their original positions as shown in FIG. 3d. The process continues with the resuspension of all particles and repetition of the cycle.

Figure 4A:
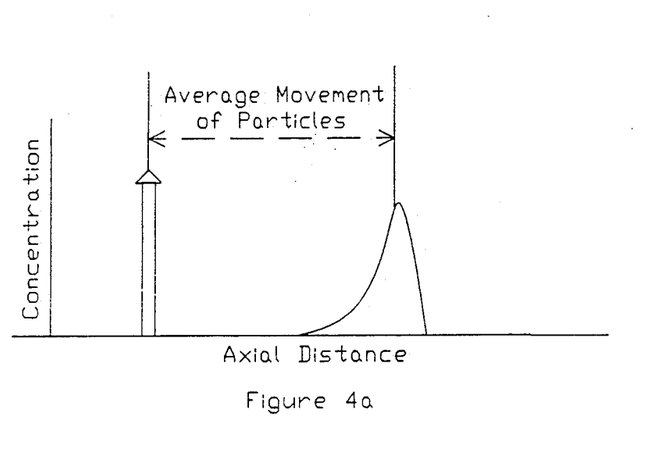
FIG. 4a shows the average movement in the batch process.
Figure 4B:
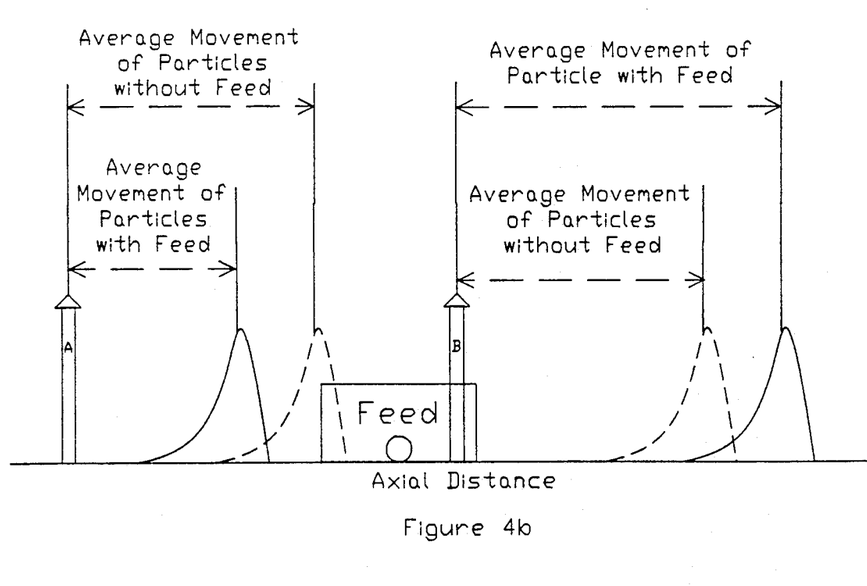
FIG. 4b shows the average movement in the continuous process.

FIGS. 4a and 4b show in schematic form the average movement of particles in the batch process (4a) and in the continuous process (4b).

Consider a pulse of particles of one type (e.g. "A" uniformly distributed in the cross section at some axial location in the tube. The particle axial concentration distribution after one cycle in a batch mode of operation (no continuous feed) is shown in FIG. 4a. The distance between the mean of the distribution and the original pulse is the average distance moved by the particles in one cycle. Dividing the average movement per cycle by the cycle duration yields the average particle drift velocity. In addition, the variance of the distribution about its means is a measure of particle axial dispersion.

For a continuous process, feed slurry is introduced (in the mid-section of the tube) periodically, e.g. after the completion of each cycle. The concept of average particle movement per cycle as defined for a batch process must be modified. Since the volume of the system is fixed, any volume of slurry entering in the middle of the tube must displace an equal volume of slurry from the two ends. Consider "A" particles to the left of the feed point; the average movement to the right is reduced by a distance equal to the feed movement in that half of the tube. For "A" particles to the right of the feed point, the average movement to the right is increased by the same amount. This concept is illustrated in FIG. 4b for two pulses A and B of "A" particles originally in the left and right section of the tube. Thus, in a continuous process, the average distance and velocity of movement are a function of the location of the particles with respect to the feed point.

To practice the invention it is necessary to set various operating conditions, such as forward and backward velocities and stroke time durations, and waiting periods, if any, into the controlling software. The basic physical parameters and operational conditions for fractionating particles based on the differences in their sedimentation rates are as follows:

L, the tube length, cm $t_{SL}$, the sedimentation time for the "large" (faster sedimenting) particles, s $t_{SS}$, the sedimentation time for the "small" (slower sedimenting) particles, s $t_F$, the time of duration of the forward stroke, s $t_{FB}$, the time of duration of the waiting period after the forward stroke, s $t_B$, the time of duration of the backward stroke, s $t_{BM}$, time of duration of the waiting period after the backward stroke, s $t_M$, the time of duration of the make-up stroke, s $u_F$, velocity of the forward stroke, cm/s $u_B$, velocity of the backward stroke, cm/s $u_M$, velocity of the make-up stroke, cm/s $x_F$, ($\geq 0$) the forward stroke distance relative to 0, cm $x_B$, ($\leq 0$) the backward stroke distance relative to 0, cm $x_M$, ($\geq 0$) the make-up stroke distance relative to 0, cm the tube length and sedimentation velocities must be determined for a desired separation, and other processing parameters are found from a combination of modeling and empirical studies, as will be described below.

Selection of Processing Parameters

We explain next an organized procedure for selecting values of the process parameters in the three step sequence to achieve a desired separation. Those trained and skilled in separation processes will readily be able to adapt the procedure to other sequences. An example involving a binary mixture of particles is used to illustrate the procedure. The procedure is described first for batch operation, and then its extension to continuous flow processes is discussed.

The procedure consists of four tasks. Task 1 is problem specification, including determining particle sizes and densities, fluid viscosity and density, and definition of the desired separation. Task 2 makes preliminary estimates of the process parameters based on simple calculations and rules to be described shortly. In task 3 these preliminary estimates are tested in a computer model which simulates one cycle of operation, and the results of the simulation are extended by simple auxiliary calculations to predict the overall performance of the process. By modifying the parameter estimates iteratively, the predictions made in task 3 are brought into conformity with the desired separation. In task 4 the process parameters found in task 3 are tested experimentally and adjusted to achieve the desired separation results. Within tasks 3 and 4 specific rules are followed to guide the iterative determination of suitable process parameter values. Although task 3 can be omitted, and the preliminary process parameter estimates from task 2 can be used directly as the starting point for experimental iterations in task 4, skipping task 3 generally results in a greater number of experiments being needed in task 4 and more work overall. The use of all four tasks is generally desirable to minimize the effort needed to achieve suitable process parameter values.

Task 1—Problem Specification

Obtain the size distribution and density of particles to be separated. Particle sizes can be obtained from many commercially available instruments such as the Sedigraph particle size analyzer, Coulter Counter, and Brookman light scattering instruments. Particle densities can be measured using sink-float or gravimetric methods. In many instances particle density values are available in standard references.

Obtain the viscosity and density of the working fluid at the operating temperature. For most common fluids this data is available in standard references such as the CRC Handbook of Chemistry and Physics.

Define the desired cut point and desired sharpness of separation. For particles of uniform density, the cut point can be specified in terms of particle sizes or sedimentation rates; e.g., "particles larger than 30 microns are desired in one product and particles smaller than 30 microns are desired in the other product", or "particles which sediment faster than 2 cm/s are desired in one product and particles which sediment slower than 2 cm/s are desired in the other product". The sharpness of separation is specified by statements such as "not more than 10% of the particles in the faster sedimenting population shall be particles with sedimentation rates less than 1.8 cm/s, and no more than 15% w of the particles in the slower sedimenting fraction shall have sedimentation rates greater than 2.3 cm/s", or "no more than 10% w of the particles in the larger particle product mixture shall be less than 29 microns in size, and no more than 15% w of the particles in the smaller particle product mixture shall be larger than 33 microns in size". For particles which vary in size as well as density, the cut point and sharpness of separation criteria are best expressed in terms of sedimentation rates such as stated above.

Task 2—Preliminary Estimates of Processing Parameters

The three step cycle consists of a forward or rightward motion (F), followed by a backward or leftward motion (B) and finally a forward "make-up" motion in the rightward direction (M). Between the forward and backward strokes there is a waiting period (FB), and between the backward and make-up strokes there is another waiting period (BM). At the beginning of each cycle all particles are uniformly suspended within each tube cross section.

The example used to illustrate the procedure is the batch separation of a mixture of polystyrene beads containing equal weights of two sizes of particles, 387 microns ("large") and 254 microns ("small"). The separation occurs in a tube of circular cross section, i.d. 0.95 cm, L=26 meters. The resuspension mechanism resuspends the particles randomly within each cross section. The density of the polystyrene beads is 1.03 g/cm$^3$. The working fluid is water at room temperature, density 1.00 g/cm$^3$ and viscosity 0.009 poise. For simplicity we confined our analysis to the vertical motion of particles in the center plane of the tube; a more precise analysis for the entire tube can be done by those familiar with the art of particle processing technology, but this degree of refinement is unnecessary to achieve reasonable process parameter estimates.

Calculate the time for complete sedimentation of particles through a distance equal to the diameter of the tube, using the appropriate drag law: Strokes, Intermediate, or Newton. For the example at hand, the sedimentation Reynolds number is less than one, so Stokes' law is appropriate. The sedimentation velocity $u_S$:

$$u_S = \frac{(\rho_p - \rho_f) g d_p^2}{18\mu}$$

For a specific separator tube, binary mixture of particles, and fluid, the quantities L (tube length), $t_{SL}$ (time of sedimentation of the large particles through a tube diameter), and $t_{SS}$ (time of sedimentation of the small particles through a tube diameter) are known. In the example, L=2,600 cm, $t_{SL}$=3.5 s, and $t_{SS}$=8.1 s.

There are sixteen (16) process parameters to be determined, but only six (6) are independent. Many sets of six parameters can be chosen as independent; a convenient choice is N=L/(−$x_B$)=Number of cycles needed for fluid to traverse the length of the tube, dimensionless $R_1$=$x_F$/(−$x_B$)=Ratio of forward stroke length, step 1, to backward stroke length, step 2, dimensionless $R_2$=($t_F$+$t_{FB}$)/$t_{SL}$=Ratio of the sum of the durations of step 1 and the waiting period between steps 1 and 2 to the sedimentation time for the large particles, dimensionless $R_3$=$t_{FB}$/$t_F$=Ratio of the duration of the waiting time between steps 1 and 2 to the duration of step 1, dimensionless $R_4$=$t_{BM}$/$t_B$=Ratio of the duration of the waiting time between steps 2 and 3 to the duration of step 2, dimensionless $u_M$=Velocity of the make-up stroke, step 3, cm/s The values of these six independent process parameters are determined from the following guidelines:

(1) N is chosen in the range of 10<N<∞. For relatively easy separations (($t_{SL}$/$t_{SS}$)>3), N can be relatively small, say 10. For relatively difficult separations (1<$t_{SL}$/$t_{SS}$<3/2), N should be chosen to be relatively large, say 100 or more. A reasonable default value is N=50. In the example, N=54.

(2) $R_1$ should be chosen such that ¼<$R_1$<½. A reasonable default value is $R_1$=⅓. In the example, $R_1$=⅓.

(3) $R_2$ should be chosen such that ¼<$R_2$<½. A reasonable default value is $R_2$=5/12. In the example, $R_2$=5/12.

(4) $R_3$ should be chosen such that 0<$R_3$<10. A reasonable default value is $R_3$=3/2. $R_3$→0 for difficult separations, and $R_3$→10 for easy separations. In the example, $R_3$=3/2.

(5) $R_4$ should be chosen such that 0<$R_4$<∞. A reasonable default value is $R_4$=½. $R_4$→0 for difficult separations, and $R_4$→∞ for easy separations. In the example, $R_4$=0.1.

(6) Select any reasonable value for $u_M$ subject to the constraint that the make-up flow stroke, step 3, should be laminar to avoid turbulent resuspension of sedimented particles. In the example, $u_m$=8 cm/s, corresponding to a flow Reynolds number of 850, safely within the laminar flow regime ($N_{Re}$<2,300).

The remaining dependent process parameters ($x_F$, $x_B$, $x_M$, $t_F$, $t_{FB}$, $t_B$, $t_{BM}$, $t_M$, $u_F$, $u_B$) are calculated from the known quantities L, $t_{SL}$, $t_{SS}$, and the independent process parameters N, $R_1$, $R_2$, $R_3$, $R_4$, and $u_M$ using the relationships $x_F$=−$x_B$*$R_1$ (follows from definition of $R_1$). In the example, $x_F$=16 cm $x_B$=−L/N (follows from definition of N). In the example, $x_B$=−48 cm.

$x_M$=−$x_F$−$x_B$ (follows from $x_F$+$x_B$+$x_M$=0, requirement that there be zero net fluid flow). In the example, $x_M$=32 cm.

$t_F$=$t_{SL}$*$R_2$/(1+$R_3$) (follows from definitions of $R_2$ and $R_3$). In the example, $t_F$=0.6 s.

$t_{FB}$=$t_F$*$R_3$ (follows from definition of $R_3$). In the example, $t_{FB}$=0.9 s.

$t_B$=($t_{SS}$−$t_{SL}$*$R_2$)/(1+$R_4$) (follows from definition of $R_2$ and $R_4$, plus the requirement that all particles be settled at the end of the waiting period following the backward stroke, step 2, i.e., $t_{SS}$=$t_F$+$t_{FB}$+$t_B$+$t_{BM}$). In the example, $t_B$=6.0 s.

$t_{BM}$=$t_B$*$R_4$ (follows from definition of $R_4$). In the example, $t_{BM}$=0.6 s.

$t_M$=$x_M$/$u_M$ (definition of velocity $u_M$). In the example, $t_M$=4 s.

$u_F$=$x_F$/$t_F$ (definition of velocity $u_F$. In the example, $u_F$=26.7 cm/s.

$u_B$=$x_B$/$t_b$ (definition of velocity $u_B$). In this example, $u_B$=−8.0 cm/s Next, the value of the dependent process variable $u_B$ is checked to test whether the axial flow in the backward stroke, step 2, is turbulent or laminar. Strongly turbulent flow in the backward stroke is undesirable because it tends to cause resuspension of the particles sedimented prior to this motion. Since these sedimented particles are predominantly large, their resuspension and consequent leftward motion is undesirable. If the flow regime during the backward stroke, step 2, is turbulent, N should be increased, or the tube diameter decreased. Turbulent flows are acceptable during the forward stroke, step 1.

In the example, the flow Reynolds Number during the forward stroke, step 1, is 2,820, just above the laminar-turbulent transition of ~2,300. This is acceptable. The flow Reynolds Number during the backward stroke, step 2, is 850, safely in the laminar regime.

Task 3—Computer Simulation and Prediction of Process Performance

Using the process parameter values arrived at in Task 2, a computer simulation of a cycle is made for an initial condition consisting of a mixture of large and small particles uniformly distributed in one cross section. In the simulation, particle axial motions coupled with their sedimentation rates are modeled from first principles and calculated. The particle axial velocity is assumed at all times to match the axial velocity of the surrounding fluid. Standard expressions are used for axial velocity profiles. For a tube of circular cross section, $$u = u_{max}(1-(r/R)^2) \text{ laminar flow}$$

$$u = u_{max}(1-(r/R))^{1/7} \text{ turbulent flow}$$

Integrated expressions for particle trajectories over a cycle for all possible initial positions of a particle in the cross section for laminar and turbulent flows can be found in Palepu et al [10]. In order to obtain accurate average movements of particles over a cycle, populations of 100 or more large and small particles are used. In addition to determining the mean axial motions of the populations, the variance $\sigma^2$ of the populations in the axial direction about their means is evaluated. The simulation is readily performed using a personal computer. A sample program written in APL is shown as FIG. 5.

For batch separations, once means movement per cycle, $\bar{x}$, and variance, $\sigma^2$, for both the large and small particles is determined, the steady state concentration profiles are given by $$C = (|U|/D) * \text{Exp}(-|U||Z|/D)$$

where C is normalized by the total mass of the large (small) population, and is expressed on a per unit axial distance basis; U is a drift velocity—the net axial movement of the large (small) particles per cycle, $\bar{x}$, divided by the total cycle time, $t_C$. D is the effective axial dispersion coefficient of the large (small) particles, calculated from the variance of the large (small) particles and Z is the axial position along the length of the tube, measured from the right (left) end. Explicit formulas [10] for U and D are $$U = \bar{x}/t_C$$

$$D = \sigma^2/(2 \cdot t_C)$$

In the example, $t_C = t_F + t_{FB} + t_B + t_{BM} + t_M = 12.1$ s; $\bar{x}_L = 11.1$ cm, $\sigma_L^2 = 58$ cm$^2$, $U_L = 0.92$ cm/s, $D_L = 2.4$ cm$^2$/s; $\bar{x}_S = 11.0$ cm, $\sigma_S^2 = 948$ cm$^2$, $U_S = -0.91$ cm/s, $D_S = 28.2$ cm$^2$/s.

For the example at hand, the steady state concentration profiles are very acceptable. They show essentially complete separation of the large particles at the right end of the tube (99+% in rightmost 13 cm of the tube), and of the small particles at the left end of the tube (99+% in the leftmost 150 cm of the tube).

In case the separation predicted by the simulation is unsatisfactory, the process parameters are adjusted iteratively within Task 3 until suitable values are found. General guidelines for the effects of each of the independent process parameters are as follows:

N affects the sharpness of separation and the total production rate. Increasing N favors sharper separation at the cost of lower production rates.

The parameters $R_1$, $R_2$, and $R_3$ affect the degree of large particle rightward movement. Increasing $R_1$, $R_2$ and/or $R_3$ favors better concentration of the large particles at the right end of the tube, but reduces the concentration of small particles at the left end of the tube. Decreasing $R_1$, $R_2$ and/or $R_3$ has the opposite effect.

The parameter $R_4$ affects the degree of small particle leftward movement. Increasing $R_4$ enhances the concentration of small particles on the left, while degrading the concentration of large particles on the right. Decreasing $R_4$ reduces the concentration of small particles on the left, while increasing the concentration of large particles on the right.

Figure 6:
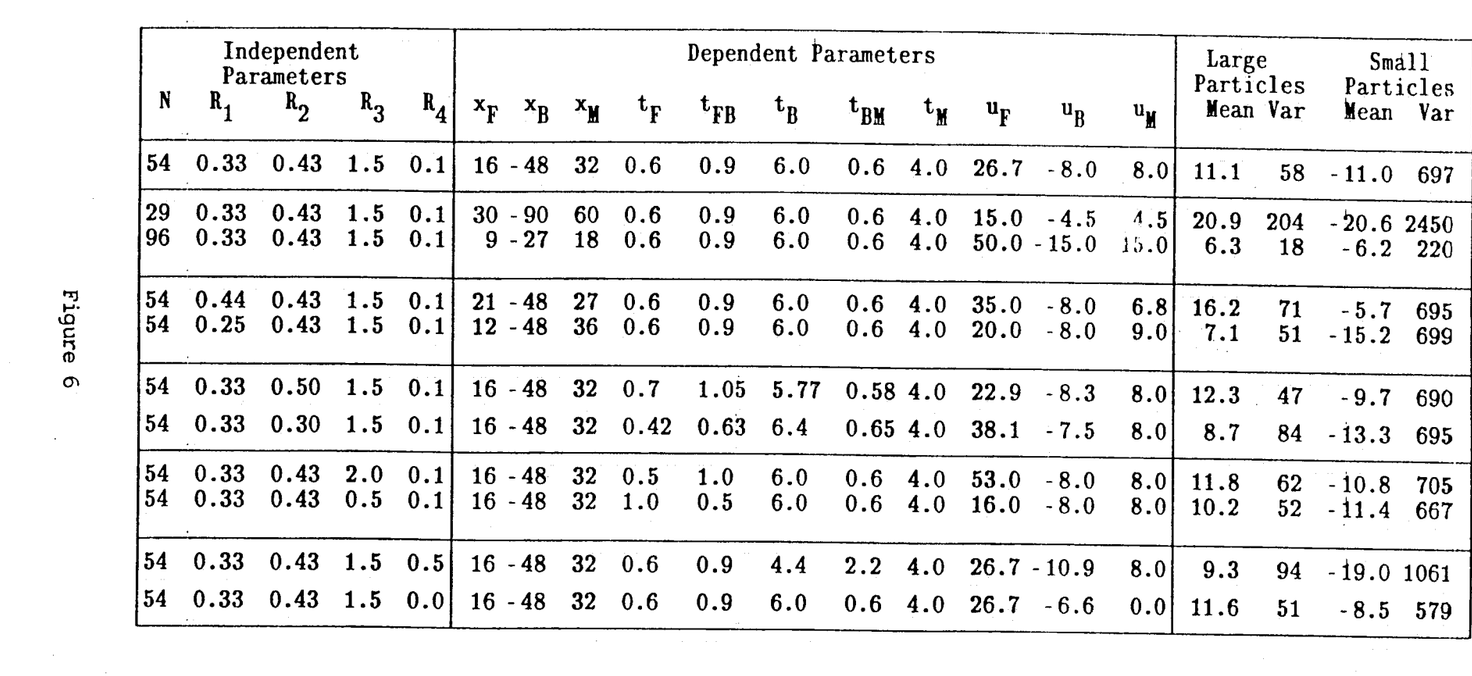
FIG. 6 shows simulation results of separator performance for various values of process parameters.

FIG. 6 shows simulation results of separator performance for various values of process parameters. Line one is for the initial choice of parameters from Task 2. Succeeding lines show the effects of perturbing the independent process parameters (N, $R_1R_2$, $R_2$ and $R_4$) one at a time. All of the perturbed sets of parameter values are suitable. The choice of the best set of independent process parameters depends on the specific separation objectives desired.

Task 4—Experimental Refinement of Process Parameters

The process parameter values from task 3 are tested experimentally, and adjusted iteratively to optimize performance. The same logic and guidelines used in Task 3 are used, but with experimental results substituted for numerical simulations.

Extension to Continuous Flow Processing

The extension of batch operations to continuous processing is readily accomplished by adding feed slurry at an appropriate position along the length of the separator tube, withdrawing product slurry rich in large particles at the right end of the tube, and withdrawing product slurry rich in small particles at the left end of the tube. The feed additions and product withdrawals can be continuous or periodic. A convenient method of adding feed and withdrawing products is to add a pulse of feed slurry upon completion of each cycle after resuspension has been completed. Since the volume of the tube is fixed, the feed slurry displaces an equal volume of product slurry from the two ends; the relative amounts of the two product slurries are readily controlled by flow resistances or valves at the ends of the tube.

In the typical situation where the separation is substantially complete, the feed can be introduced anywhere in the middle section of the tube where particle concentrations are substantially zero in the batch mode of operation. When the separation is difficult, both types of particles exist along the length of the tube in batch operation. In this case it is best to add the feed at the position where the particle compositions in the tube match the feed composition, as is normally done in conventional separation processes such as continuous countercurrent distillation.

The volume of feed introduced must be limited in order to maintain good separation. A simulation model for continuos operation, including the feed and withdrawal steps, enables the calculation of process performance in the continuous flow mode of operation. This model is similar to the batch model discussed above; the feed addition and product withdrawal steps are added. To those skilled in the art of separation processes, the writing of such a program will be obvious, based on the earlier discussion of the batch simulation model. If the continuous flow version of the model predicts that the average motion of the large particles in the portion of the tube to the left of the feed point is leftward, then the amount of feed flowing into the left portion of the tube is excessive. Similarly if the model predicts that the average motion of the small particles in the portion of the tube to the right of the feed point is rightward, then the amount of feed flowing into the right portion of the tube is excessive. If either of these situations occur, the difficulty can be overcome by distributing the feed more favorably between leftward and rightward directions, by reducing the amount of feed, or by adjusting the process parameters in order to increase the mean movement of particles in the batch mode of operation. One or more of these methods is chosen and used to overcome the above mentioned difficulty by using procedures similar to those used in countercurrent distillation to overcome analogous problems. As with the batch mode of operation, once acceptable process parameters and feed amounts are found by simulation of the continuous process, experiments are performed, and if necessary, refinements are made following the same guidelines as used in Task 3.

Use of the Process and Apparatus for Countercurrent Extraction Process

The particle fractionation process heretofore described can be readily adapted as a countercurrent solid-fluid contacting process. Such processes are used for extracting soluble components from particles into a fluid solvent, and also for washing components from surfaces of particles. Some examples are extracting soluble components from coffee beans or tea leaves into water or carbon dioxide. Another example is washing of surface impurities from silica sand.

The countercurrent contacting can be conducted in the same apparatus described heretofore by modifying the fractionation cycle and eliminating the slurry feed from the mid-section of the separator tube. Consider two containers joined by a separator tube. Let the container at the left end receive fresh solids and the container at the right end receive fresh solvent. Fluid extract is removed from the left container and spent, washed solids are removed from the right container. The countercurrent movement of solids to the right and solvent to the left within the separator tube is brought about by a two step cycle. Particles are resuspended prior to the start of each cycle. The two step cycle consists of a rightward (forward) flow plus an optional waiting period followed by a leftward (backward) flow plus an optional waiting period. The rightward step carries fluid plus the suspended particles to the right. To achieve a net flow of fluid to the left, the fluid flow during the leftward step must exceed the fluid flow during the rightward step. To size the separator tube and design the process cycle, the following steps are used:

(1) Select the desired extract concentration.
(2) Determine the fluid flow to solid flow ratio by making an overall mass balance as is done in a conventional countercurrent extraction process.
(3) Specify the solids (or fluid) flow rate and calculate the fluid (or solids) flow rate using the fluid to solids ratio determined in (2).
(4) Design the two step cycle in order to achieve the desired solids and fluid flow rates. The solids flow rate is determined from a simulation model analogous to the one described earlier for fractionating particle mixtures. Such a model will determine the average drift velocity and axial dispersion coefficient of the particles as a function of the process parameters for the two step cycle. Process parameters also determine the net liquid flow to the left. Leftward flow velocities should be small enough not to disturb the sedimented particles.
(5) Determine the length of the separator tube by developing and solving the appropriate model based on material balances incorporating mass transfer rates during the periods when particles are in suspension. Such models and solution techniques are well known in the literature for the design of conventional countercurrent solid-fluid extraction processes.
(6) Test and refine the process design and parameters experimentally.

Use of Other Than Gravitational Fields for Separation and Resuspension

Thus far, the invention has been described in terms of a gravitational field causing sedimentation of particles. As will be clear to those familiar with the laws of physics, other fields can also be used, such as centrifugal, electric, and magnetic. Centrifugal fields can be applied broadly to all particles differing in density from the fluid. Electric and magnetic fields can be applied when the particles are charged or magnetically susceptible, respectively. The sedimentation rates of particles under these fields are calculated or determined experimentally by methods well known in the art. The method of particle fractionation disclosed earlier for gravitational fields is equally applicable with other fields whenever the particles exhibit different sedimentation rates. The flow independent methods of particle resuspension described earlier for gravity fields are also applicable to other fields: For example, inverting the separator tube with respect to the applied field, or using acoustic energy of sufficient strength to overcome the effects of the applied field. In the case of an electric field, the inversion can be accomplished conveniently by reversing the voltage. A combination of fields can also be advantageously used; for example, magnetic and centrifugal fields can be used in conjunction advantageously by maintaining the centrifugal field and switching the magnetic field off and on to alternately sediment and resuspend the particles.

Field inversion is an attractive method of achieving complete resuspension almost instantaneously without moving the particles or the separator tube; the sedimented particles without a change in their position are immediately able to begin resedimenting in the next cycle. It will of course be seen that "field inversion" encompasses the original method disclosed herein for the gravitational field, in which the direction of the field is also reversed with respect to the tube, but by inverting the tube rather than the field.

EXPERIMENTAL EXAMPLES

Batch Experiment

The first experiment was a batch separation of a mixture of two types of plastic beads slurried in equal weight fractions in water. Dowex ion exchange resin beads with a mean diameter of 137 $\mu$m (125-149 $\mu$m range), density of 1.24 g/ml and mean settling velocity of 0.245 cm/s (range 0.204-0.290 cm/s) were the "A" particles. Polystyrene beads with a mean diameter of 254 $\mu$m (210-297 $\mu$m range), density of 1.03 g/ml and mean settling velocity of 0.105 cm/s (range 0.072-0.144 cm/s) were the "B" particles. The total concentration of particles in the slurry was 5% by volume. Initially, the slurry occupied the middle 50% of the tube length. The "A" particles were dyed brown and the "B" particles blue, to facilitate observations in the tube.

Useful process operating conditions were estimated for the three step separation cycle described hereinabove, by a method equivalent to the one herein entitled "Selecting Processing Parameters". See FIG. 7, which shows process conditions for batch and continuous experiments. With these conditions, the process reached steady state in 240 cycles. All of the "A" particles (Dowex ion exchange resin beads) were concentrated at the right end of the tube and all the "B" particles (Polystyrene beads) were concentrated at the left end of the tube. Essentially all (99%) of the "A" particles were concentrated in the rightmost 38 cm of the 2600 cm long separator tube and essentially all of the "B" particles were concentrated within the leftmost 105 cm of the tube. We observed no "A" particles (brown) among the "B" particles (blue) or vice versa. Separation was complete and the concentrations at the extreme ends were very high (>80% by volume of compacted slurry).

Continuous Flow Experiment

A experiment was performed using two different size polystyrene particles in a continuous mode of operation. "A" and "B" particle mean diameters were 387 $\mu$m (354-420 $\mu$m range) and 254 $\mu$m (210-297 $\mu$m range). Their mean settling velocities were 0.245 cm/s (range 0.205-0.288 cm/s) and 0.105 cm/s (range 0.072-0.144 cm/s) respectively. Density of both types of particles was 1.03 g/ml. "A" particles were dyed red and "B" particles were dyed blue. Particle concentration in the slurry feed was 6.5% by volume. Feed slurry containing the particle mixture was introduced in the middle of the tube and product slurry streams were withdrawn from the two ends after every three step separation cycle.

Figure 7:
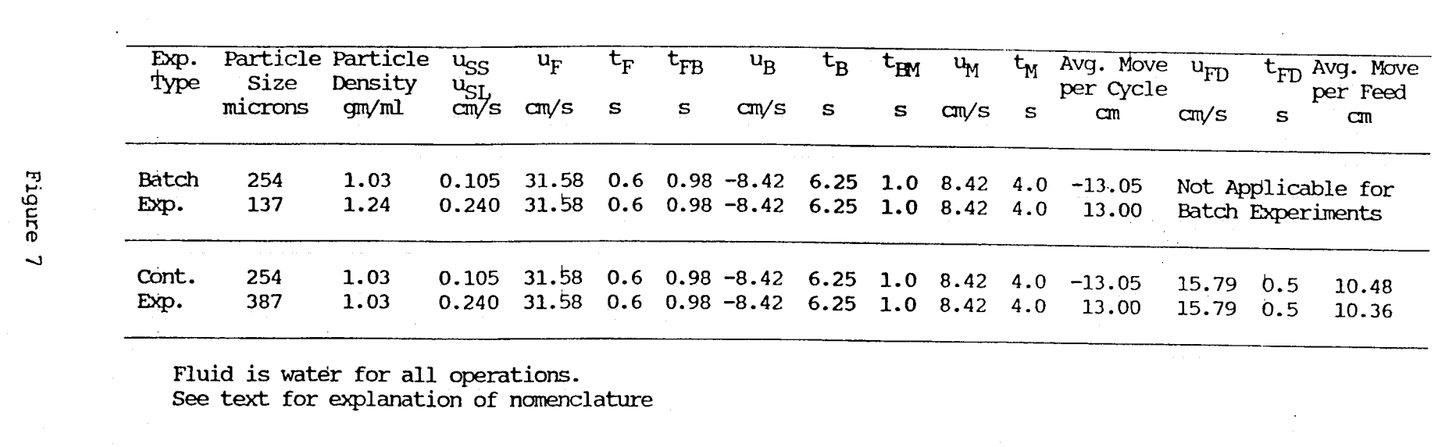
FIG. 7 shows process conditions for batch and continuous experiments.

Useful process conditions were again estimated; see FIG. 7. Steady state was reached after 135 cycles with "A" particles moving rightward and "B" particles moving leftward. Particle concentrations in the tube changed from a mixed state at the feed point to essentially pure "A" (red) and "B" (blue) particles at the right and left ends, respectively, of the tube. No red particles were observed in the blue product stream or vice versa.

Concluding Remarks

The process of our invention has advantages over classical methods of fractionating such as screening and flotation. When compared to screening, the new process allows smaller particles to be processed, and enables narrower and more precise cuts. A practical lower limit on the size of the smallest particle which can be separated by screening is usually considered to be about 37 μm (400 mesh), although special screens can be obtained down to 30 μm (500 mesh). In contrast, the new process, without extensions, can handle mineral particles as small as 10 μm under gravitational field. It can process mineral particles down to 1 μm under centrifugal fields. Normally, screening is capable of producing fractions ±10% in size; the new process is capable of ±1%. In addition, the process is continuously adjustable as to cut point and sharpness of separation without hardware changes. It is rugged and avoids screen wear. When compared to flotation, it is less subject to upsets due to subtle feed variations, consumes no reactants, and its performance is more predictable.

One very attractive feature of the process is that production rate can be traded off against sharpness of separation without any equipment modifications. The trade off is done wholly by changing user selectable operating variables. In the process, small axial velocities and flow distances favor sharp separations while large axial velocities and flow distances favor high production rates. This flexibility allows the number of separation stages in the same equipment to be varied from a few to many hundreds.

The process is broadly applicable. Several potential uses include: (1) Preparation of monodisperse particle size standards, (2) Production of narrowly sized fine ceramic particles, (3) Fractionation of metal oxide crystallites used in superconductivity research, (4) Fractionation of electronic materials, e.g. barium titanate, (5) Ore beneficiation, (6) Coal cleaning, (7) Production of monodisperse packings for use in laboratory and production scale chromatographic separation of pharmaceuticals, and (8) Separation of bacteria or mammalian cells in protein production. These uses span a very broad range from minerals to biologicals.

Our invention has been described in detail with particular emphasis on the preferred embodiments there of, but it should be understood that other variations within the spirit and scope of the invention may occur to those skilled in the art to which our invention pertains.

What is claimed is:

1. Apparatus for fractionating a first and a second particle in a fluid, said first particle having a first sedimenting rate and said second particle having a second sedimenting rate less than said first sedimenting rate, said apparatus comprising a tube having a generally lengthwise axis and being adapted to contain said mixture of particles in said fluid, said first and second particles having, respectively, first and second original axial positions, and said tube being so oriented that said particles are urged toward an inner surface of said tube;

first flow generation means to cause a first flow of said fluid in a first direction along said axis;

first flow control means to impose a first velocity and a first time period upon said first flow such that said first particle will be carried a substantial distance in said first direction from said first original position, and then will sediment at said inner surface during said time period of said first flow but said second particle will not sediment;

second flow generation means to cause a second flow of said fluid in a second direction opposite said first direction;

second flow control means to impose a second velocity and a second time period upon said second flow such that said first particle will remain sedimented and said second particle will be carried by said second flow a substantial distance in said second direction from said second original position, and then will sediment at said inner surface; and resuspension means to resuspend said first and second particles without substantially dispersing them axially from their sites of sedimentation, said resuspension means comprising means independent of axial flows.

2. The apparatus of claim 1 and in which said first and second flow control means comprise first and second stepping motors and first and second solenoid operated pinch valves controlled and operated by a computer.

3. The apparatus of claim 1 and in which said first and second flow control means are capable of providing, respectively, first and second waiting periods of substantially no fluid flow at the ends, respectively, of said first and second flows.

4. Apparatus for processing a mixture of particles and fluid, comprising a tube having two ends, having a lengthwise axis and being adapted to contain said mixture;

receiving means at each said end of said tube to receive components of said mixture from said tube;

feed means to feed components of said mixture into said tube;

flow means capable of generating a flow of said mixture in said tube at any desired one of a plurality of velocities including zero towards either said end of said tube, for any desired one of a plurality of time periods;

flow control means capable of operating said flow means so as to generate a periodic sequence, each step of said sequence consisting of a flow; and resuspension means capable of resuspending sedimented particles, without substantial axial dispersion, during a time of zero flow after each period of said periodic sequence.

5. The apparatus of claim 4 and in which said particles tend to move in a direction with respect to said tube in response to a field, and said axis is perpendicular to said field; and said resuspension means comprises means to invert the direction of said field with respect to said tube causing said particles to tend to move in the reverse of said direction with respect to said tube.

6. A process for separating a first particle and a second particle in fluid, said first particle having a first sedimentation rate and said second particle having a second sedimentation rate less than said first sedimentation rate, said process comprising (a) introducing said particles and fluid into a tube having a lengthwise axis so that said first particle is at a first original position and said second particle is at a second original position along said axis, and said tube being oriented such that said particles tend to undergo sedimentation onto an inner surface of the tube;

(b) inducing a first flow, in a first direction, upon said fluid and particles before said particles have undergone sedimentation, so that both particles are carried a substantial distance in said first direction from their respective original positions;

(c) inducing a second flow, in a second direction opposite to said first direction, upon said fluid and any unsedimented particles, said first and second flows being of such velocities and time periods such that said first particle tends to sediment at a substantial distance in said first direction from first original position and said second particle tends to sediment at a substantial distance in said second direction from said second original position;

(d) resuspending said particles without substantially dispersing them from their sites of sedimentation by means comprising resuspension means independent of axial flows; and (e) repeating said process, in the order given, beginning with step (b), so that said first particle is moved in said first direction and said second particle is moved in said second direction.

7. The process of claim 6 and further comprising inducing a third flow in said first direction, after said second said particle has sedimented but before step (d), sufficient to bring the net axial flow to zero.

8. The process of claim 6 and further comprising the step of permitting said first particle to sediment during a period of zero fluid flow between steps (b) and (c).

9. The process of claim 8 and further comprising the step of permitting said second particle to sediment during a period of zero fluid flow between steps (c) and (d).

10. The process of claim 6 and further comprising the step of permitting said second particle to sediment during a period of zero fluid flow between steps (c) and (d).

11. The process of claim 6 and in which said particles are susceptible to a field, and step (d) comprises inverting said field with respect to the cross-section of said tube.

12. A process for moving a particle and a fluid in opposite directions along the axis of a tube having an inner wall, comprising (a) introducing said particle and fluid into said tube with said axis perpendicular to a field to which said particle is susceptible;

(b) inducing a first axial flow in a first axial direction in said tube so that said particle is carried in said first axial direction;

(c) permitting said particle to move in the direction of said field toward said inner wall and to sediment there;

(d) inducing a second axial flow, in a second and opposite axial direction in said fluid, not of sufficient velocity to suspend or to carry said particle in said second axial direction, for a sufficient time to cause a net movement of said fluid in said second axial direction;

(e) resuspending said particle without substantial axial dispersion by inverting the direction of said field with respect to the axes of coordinates affixed to the cross-section of said tube; and (f) repeating said process beginning at step (b).

13. A process for separating a first type of particles from a second type of particles, both contained in a population of particles, said first type of particles having a first sedimentation rate and said second type of particles having a second sedimentation rate less than said first sedimentation rate, said process comprising (a) introducing said particle population and fluid into a tube having a lengthwise axis so that said first type of particles occupy a first set of original positions and said second type of particles occupy a second set of original positions along said axis, and said tube being oriented such that said particle population tend to undergo sedimentation onto an inner surface of said tube;

(b) inducing a first flow, in a first direction, upon said fluid and particle population before said population has undergone sedimentation, so that both types of particles are carried a substantial distance in said first direction from their respective original positions;

(c) inducing a second flow, in a second direction opposite to said first direction, upon said fluid and any unsedimented particles, said first and second flows occurring while both types of particles are undergoing sedimentation, and said flows being of such velocities and time periods that said first type of particles are more fully sedimented before said second flow than are said second type of particles, so that a portion of said first type of particles sediments at sites removed in said first direction a substantial distance away from their said first original positions and most of said second type of particles are carried a substantial distance away from their said second original positions in said second direction;

(d) resuspending all sedimented particles without substantially dispersing said sedimented particles in the axial direction from their sites of sedimentation by means comprising resuspension means independent of axial flows; and (e) repeating said process, in the order given, beginning with step (b), so that the average axial position of said first type of particles continues to move in said first direction and the average axial position of second type of particles continues to move in said second direction.

14. A process for moving a population of particles and a fluid in opposite directions along the axis of a tube, comprising (a) introducing said particle population and fluid into said tube so that said particle population occupies a set of original positions and said tube having an axis perpendicular to a field to which said particle population is susceptible so that said particle population tends to undergo sedimentation onto an inner surface of said tube;

(b) inducing a first axial flow in a first direction in said tube so that said particle population is carried in said first direction;

(c) inducing a second flow upon said fluid and any unsedimented particles in a second direction opposite said first direction, said first and second flows being of such velocities and times that a portion of said particle population sediments at sites removed from said set of original positions by a substantial distance in said first direction, and the net movement of fluid during the said first and second flows is in said second direction;

(d) resuspending said portion of said particle population without substantially dispersing said population in the axial direction by means comprising means independent of axial flows; and (e) repeating said process, in the order given, beginning with step (b) so that the average axial position of said particle population continues to move in said first direction and the next movement of fluid continues to be in said second direction.

* * * * *